US00PP31526P2

(12) United States Plant Patent
Clark

(10) Patent No.: US PP31,526 P2
(45) Date of Patent: Mar. 10, 2020

(54) GRAPE PLANT NAMED 'COMPASSION'

(50) Latin Name: ***Vitis* L. hybrid**
Varietal Denomination: Compassion

(71) Applicant: THE BOARD OF TRUSTEES OF THE UNIVERSITY OF ARKANSAS, Little Rock, AR (US)

(72) Inventor: John Reuben Clark, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 16/350,032

(22) Filed: Sep. 17, 2018

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./205, 207
CPC ..... A01H 5/0812
See application file for complete search history.

(56) References Cited

U.S. PATENT DOCUMENTS

| | | | |
|---|---|---|---|
| PP13,309 | P2 | 12/2002 | Clark et al. |
| PP25,152 | P3 | 12/2014 | Clark et al. |
| PP25,696 | P3 | 7/2015 | Clark et al. |
| PP25,697 | P3 | 7/2015 | Clark et al. |
| PP25,726 | P3 | 7/2015 | Clark et al. |
| PP25,746 | P3 | 7/2015 | Clark et al. |

OTHER PUBLICATIONS

Clark, J.R. et al. "'Compassion' Seedless Table Grape" 2018 Hortscience 53(3):401-403.2018. https://doi.org/10.21273/HORTSCI12783-17.

Vance, A.J. et al. "Table Grape Cultivar Performance in Oregon's Willamette Valley" 2017 Journal of the American Pomological Society 71(4): 240-249.

*Primary Examiner* — Kent L Bell
(74) *Attorney, Agent, or Firm* — Quarles & Brady LLP

(57) ABSTRACT

The botanical description and specifications of a new and distinct table grape cultivar originating from a hand-pollinated cross of 'Ark. 2349' (non-patented, non-released breeding genotype; female parent) x 'Ark. 2304' (non-patented, non-released breeding genotype; male parent) is provided herein. This new table grape cultivar can be distinguished by its seedless, green berries with a crisp, firm texture and unique fruity flavor having hardy and productive grapevines adapted to the Mid-South.

3 Drawing Sheets

Latin name: *Vitis* L. hybrid.
Varietal denomination: 'Compassion'.

BACKGROUND

The new and distinct cultivar of table grape named 'Compassion' is described herein. The new cultivar originated from a hand-pollinated cross of 'Ark. 2349' (female parent; non-patented; non-released) and 'Ark. 2304' (male parent; non-patented; non-released) made in 2002. The seedlings fruited in the summer of 2006 in a vineyard near Clarksville, Ark. and one was selected for its potential as a table grape for utilization in the Mid-South and other areas of similar climate. The original vine was tested as Ark. 2932. The new cultivar is a green (white), seedless table grape which provides a significant advancement in fruit crispness and firmness beyond previous Arkansas developments along with having an exquisite fruity flavor and limited fruit cracking or skin splitting in the Arkansas environment.

SUMMARY OF THE INVENTION

The new and distinct cultivar of grapevine originated from a hand-pollinated cross of 'Ark. 2349' (non-patented, non-released breeding genotype; female parent) x 'Ark. 2304' (non-patented, non-released breeding genotype; male parent) made in 2002 near Clarksville, Ark. The seeds resulting from this controlled hybridization were germinated in a greenhouse during the winter of 2002-03. Resulting seedlings were planted in the spring of 2003 in a vineyard near Clarksville, Ark. The seedlings fruited in the summer of 2006 and one seedling, designated Arkansas Selection 2932, was selected for its potential for fresh-market production as a seedless table grape. This selection is designated as 'Compassion'.

During late 2006 and early 2007, the original plant selection was propagated asexually at the above-noted location, by rooting hardwood cuttings. A test planting of three vines was established. In all propagations, hardwood cuttings were used and the selection rooted readily from hardwood cuttings. All propagules (resulting plants) of the new cultivar have been observed to be true to type in that during all asexual multiplication, the vegetative and fruit characteristics of the original plant have been maintained. All vines planted from hardwood cutting propagation fruited in the second or third season of growth in the vineyard after planting.

Vines of the new cultivar have good growth, not being excessively vigorous and good health as exhibited by good leaf color and no to minimal disease presence. It has produced well as own-rooted plants in all testing and has not been evaluated on any rootstocks. Adaptation to the Arkansas test site is very good as winter injury and heat damage were minimal.

The health of the new cultivar is good. Vines were evaluated for presence of the following diseases: powdery mildew (*Erysiphe necator* Schw. (syns. *Uncinula necator* (Schw.) Burr., *E. tuckeri* Berk., *U. americana* Howe, and *U. spiralis* Berk. & Curt; anamorph *Oidium tuckeri* Berk.), downy mildew (*Plasmopara viticola* Berl. & de Toni.), anthrancnose (*Elsinoë ampelina* Shear), and black rot (*Guignardia bidwellii* Viala & Ravaz). The new cultivar is moderately resistant to powdery mildew, downy mildew, and anthrancnose, but susceptible to black rot. All of these diseases can be controlled by the use of available fungicides.

The new cultivar average harvest date is 22 August in Arkansas. The berries are medium (ca. 4.5 g) and elongated-oval in shape. Fruit is seedless with small residual seed traces in most years. Fruit texture is a non-slipskin type and is crisp and firm. Flavor is fruity with some muscat aspects included and average soluble solids of 20%. Fruit cracking and skin splitting is limited though some may be seen in severe rainfall pressure seasons. Medium-sized to large clusters are well-filled to tight with average cluster weight being 470 g in Arkansas. Yield average in Arkansas is 11.4 kg/vine.

The new cultivar has been named 'Compassion'.

BRIEF DESCRIPTION OF THE PHOTOGRAPHS

The accompanying photographs show typical specimens of the new variety in color as nearly true as it is reasonably possible to make in a color illustration of this character. The plants shown in these photographs are 10 year old vines.

DETAILED DESCRIPTION OF THE NEW CULTIVAR

Figure 1:
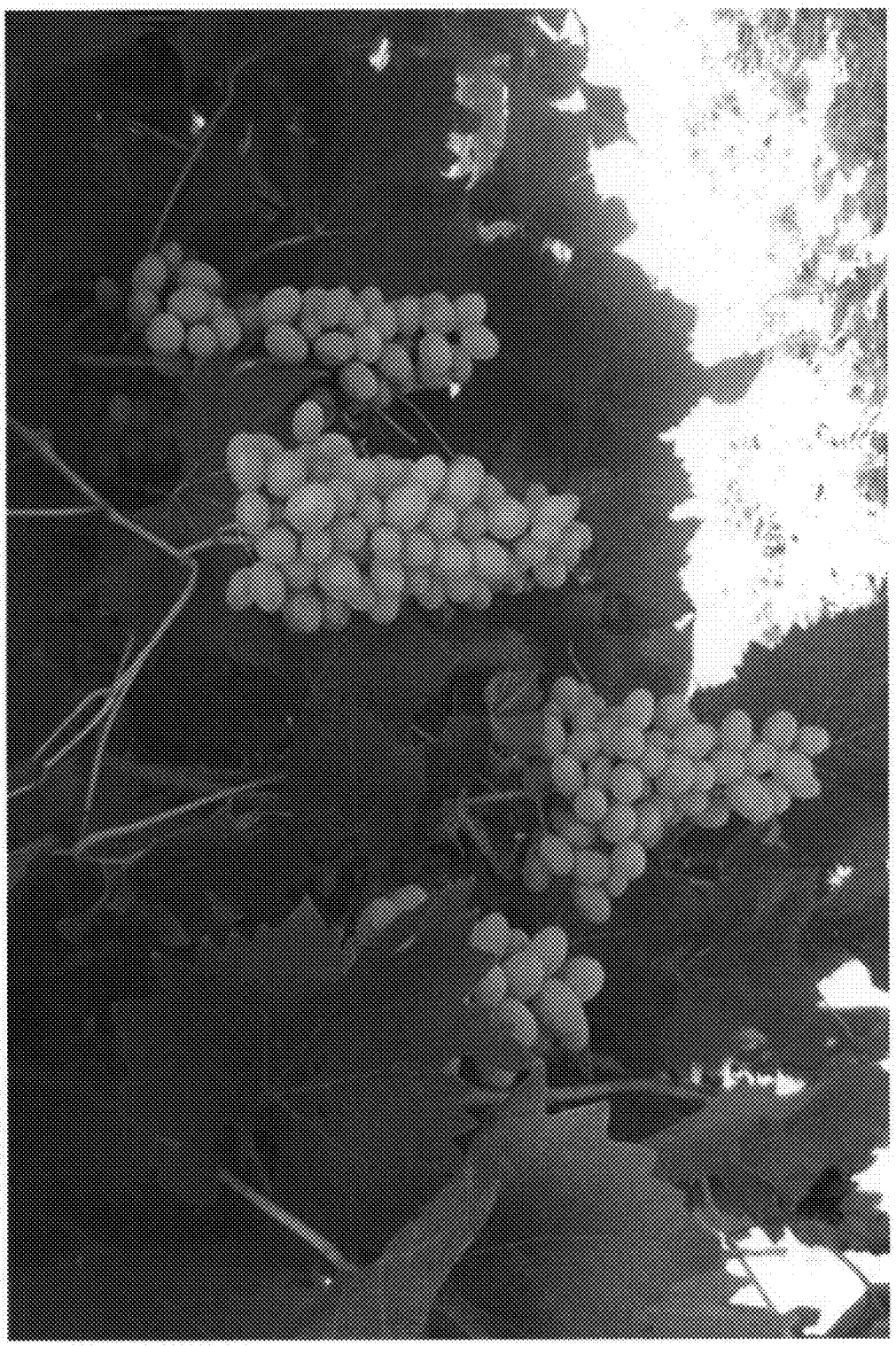
FIG. 1 is a photograph showing typical cluster of healthy fruit, near Clarksville, Ark.
Figure 2:
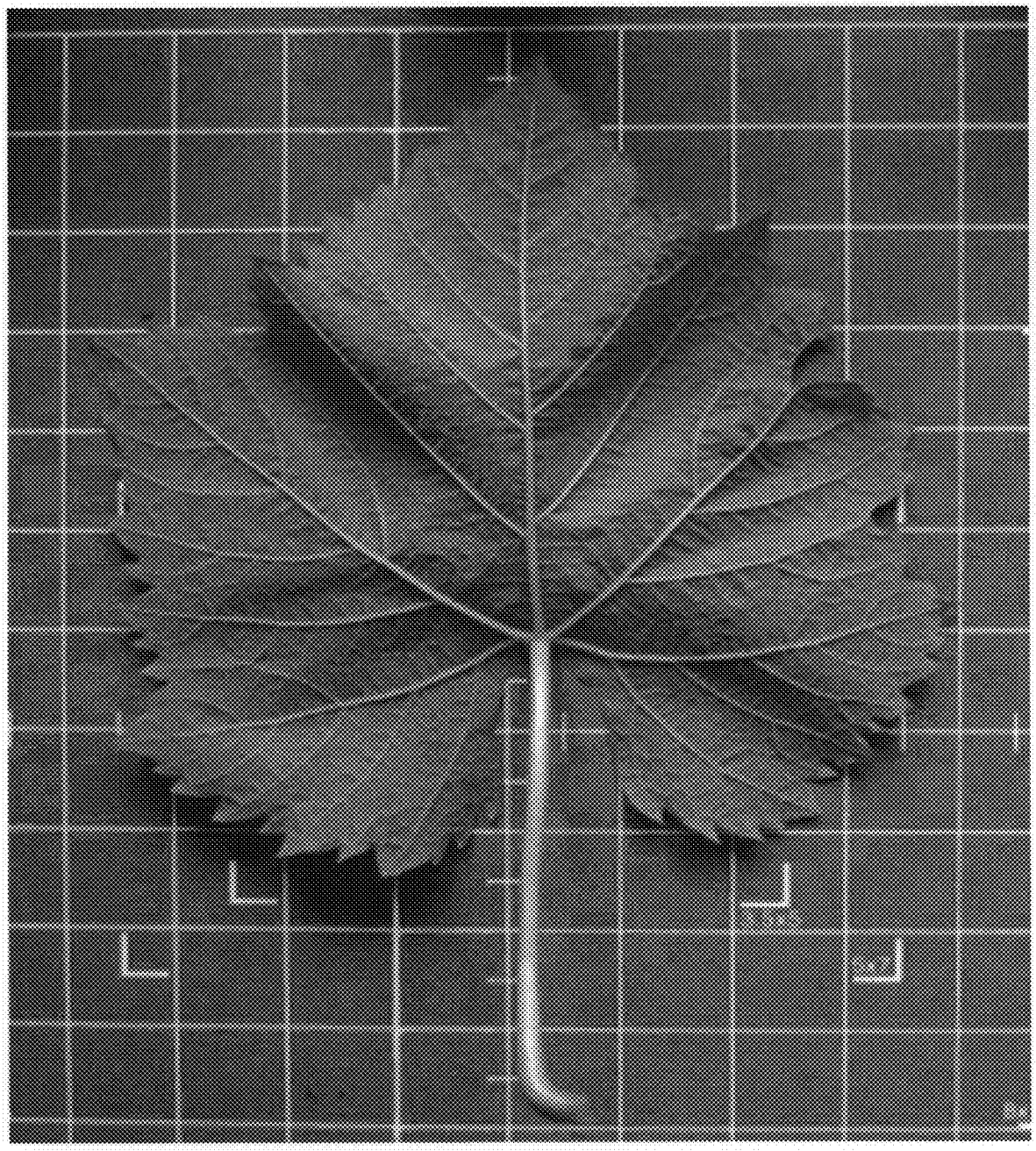
FIG. 2 is a photograph showing the leaf abaxial view, near Clarksville, Ark.
Figure 3:
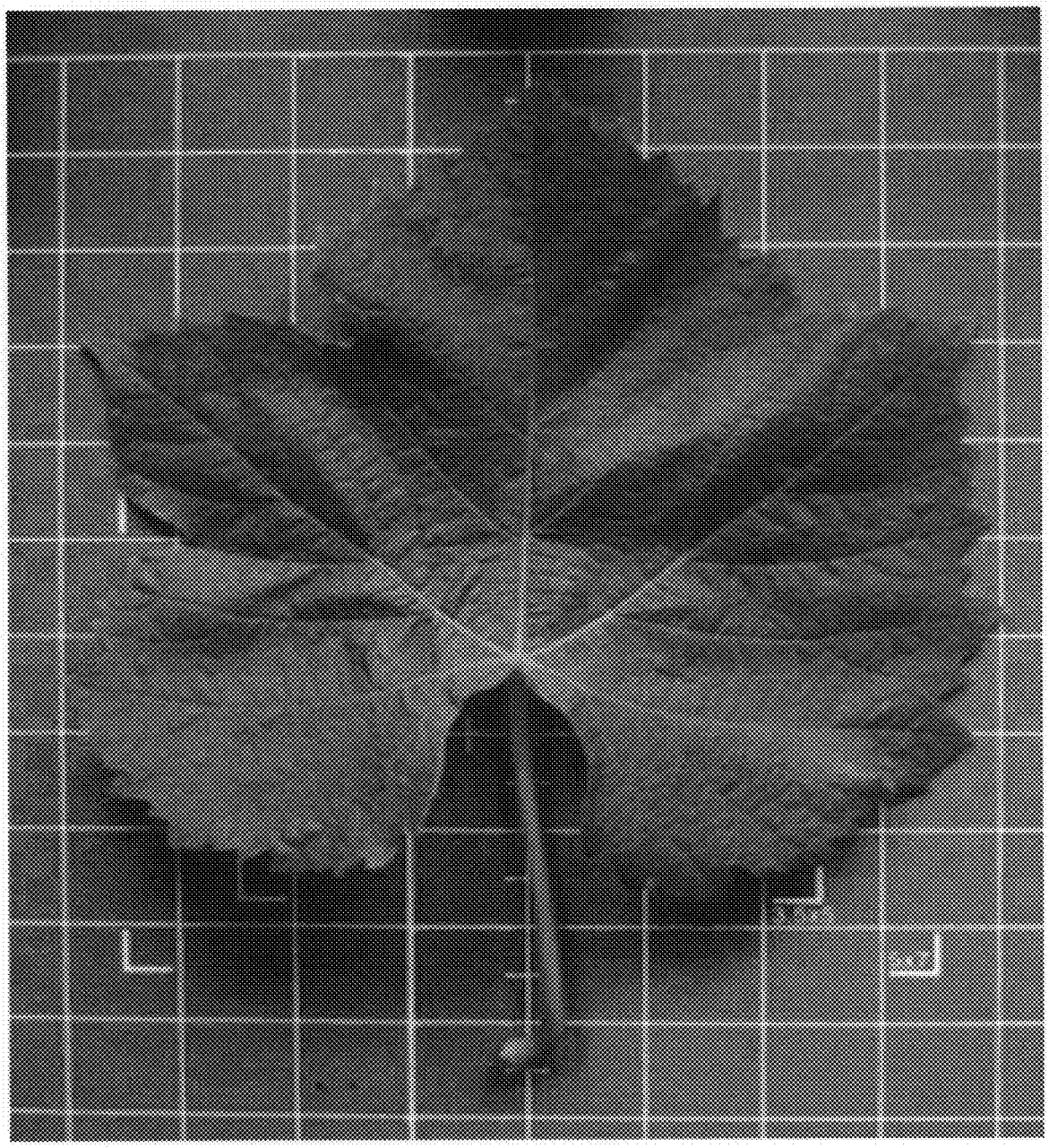
FIG. 3 is a photograph showing the leaf adaxial view, near Clarksville, Ark.

'Compassion' differs from its female parent 'Ark. 2349' in that 'Compassion' is seedless, has fruit cracking resistance, has greater yield potential and is green rather than red.

'Compassion' differs from it male parent 'Ark. 2304' in that it has fruit cracking resistance, better plant health and larger clusters.

The following is a detailed description of the botanical and pomological characteristics of the subject grapevine. Color data are presented in Royal Horticultural Society Colour Chart designations, 1986 version, second edition.

Where dimensions, sizes, colors and other characteristics are given, it is to be understood that such characteristics are approximations of averages set forth as accurately as practicable.

The descriptions reported herein are from specimens grown near Clarksville, Ark. Vines used for measurement were 10 years old and were irrigated using trickle (drip) irrigation. Vines were fertilized annually in spring with Nitrogen or complete fertilizers. No shoot or leaf thinning practice was conducted on the vines. No girdling or gibberellic acid application practices were carried out on the vines.

Vine:

*Size*.—Medium.

*Growth vigor*.—Moderate.

*Density of foliage*.—Medium-thick.

*Productivity*.—Moderate yielding, 11.4 kg/vine.

*Rootstock*.—None; own-root.

*Cold hardiness*.—Hardy to −17 ° C. (1° F.); potentially more hardy as this was the coldest temperature experienced at the test site.

Shoots (current-season canes):

*Color of shoots* (*current-season canes*).—Sun exposed side: grayed-orange group 166-A, green group 143-C (where anthocyanin present with green undercoat); shaded side: green group 143-A.

*Shoot attitude*.—Semi-procumbent.

Canes (mature, dormant, measured in winter):

*Color of mature, dormant cane*.—Base: grayed-orange group 165-B; midpoint: grayed-orange group 165-B; terminal: grayed-orange group 164-A; anthocyanin not present on mature canes.

*Texture of mature, dormant canes*.—Smooth.

*Shape of dormant canes*.—Round to lachrymiform (tear drop).

*Length of mature, dormant canes*.—Average 1.3 m.

*Diameter of mature, dormant cane*.—Base: 1.0 cm; midpoint: 0.7 cm; terminal: 0.4 cm. internode length of mature, dormant canes: base: 4.4 cm; midpoint: 8.1 cm; terminal: 4.2 cm.

*Lenticels*.—Not present on mature canes. Canes mature to tips in the fall.

Trunk:

*Diameter at* 30 *cm above soil level*.—3.4 cm.

*Shape*.—Roundish.

*Trunk straps*.—Present similar to other bunch grapes.

*Surface texture*.—Smooth with rough peeling (exfoliating) bark.

*Color*.—Inner bark color: grayed-orange group 165-A; outer bark color: grayed group 201-B with some grayed group 200-C on portions of bark.

Foliage:

*Arrangement of mature leaves*.—Simple and alternate.

*Shape of mature leaves*.—Palmate.

*Number of lobes on mature leaves*.—3.

*Petiole sinus of mature leaves*.—Open.

*Venation of mature leaves*.—Reticulate.

*Margin of mature leaves*.—Serrated with teeth medium in size.

*Teeth shape of mature leaves*.—Straight to occasional concave.

*Surface texture of mature leaves*.—Abaxial side: very mildly corrugated; adaxial side: waxy, smooth.

*Dimensions of mature leaves*.—Length: 15.7 cm; width: 16.3 cm; thickness: 0.03 cm.

*Pubescence on mature leaves*.—Abaxial side: light on veins, none to light on leaf surface; adaxial side: none.

*Color of mature leaves*.—Base abaxial: yellow-green group 146-B; base adaxial: green group 137-A; midpoint abaxial: yellow-green group 146-B; midpoint adaxial: green group 137-A; terminal abaxial: yellow-green group 146-B; terminal adaxial: green group 137-A; no anthocyanin present.

*Color of veins on mature leaves*.—Abaxial surface: yellow-green group 146-D; adaxial surface: yellow-green group 146-C; no anthocyanin on leaf veins.

*Leaf pubescence on young leaves*.—Abaxial side: lightly present veins and along edges; adaxial side: none.

*Color of young leaves*.—Base abaxial: yellow-green group 145-A (no anthocyanin present); base adaxial: yellow-green group 145-A (no anthocyanin present); midpoint abaxial: anthocyanin present, color grayed-orange group 176-C; midpoint adaxial: anthocyanin present, color grayed-orange group 176-C; terminal abaxial: yellow-green group 144-A (no anthocyanin present); terminal adaxial: yellow-green group 144-A (no anthocyanin present).

*Vein color of young leaves*.—Abaxial side: yellow-green group 147-C; adaxial side: yellow-green group 147-C; grayed-purple group 184-B (petiole end).

*Texture of young leaf veins*.—Abaxial side: heavy pubescence; adaxial side: smooth.

Petioles:

*Color of mature petioles*.—Yellow-green group 146-C; anthocyanin present on mature petioles exposed to sun with anthocyanin color Greyed-red group 182A. Anthocyanin intensity varies on petiole based on sun exposure with shaded sides having little to no anthocyanin.

*Dimensions of mature petioles*.—Length: 10.5 cm; diameter: 0.3 cm.

*Color of young petioles*.—Yellow-green group 146-B (no anthocyanin present).

Tendrils: Found beginning on the 4th node.

*Orientation*.—Opposite.

*Dimensions*.—Length: 15.9 cm.

*Texture*.—Smooth.

*Diameter*.—1.2 mm.

Color of mature tendril.—Yellow-green group 146-D. Tendril forked.

Buds (measured in dormant season):

*Number of buds on current, single-season cane*.—19.

*Dimension of dormant buds*.—Width: 0.3 cm; length: 3.6 mm.

*Shape of dormant buds*.—Pyramidal.

*Color of dormant buds*.—Grayed-orange group 177-A.

*Texture of dormant buds*.—Bumpy where scales meet.

*Bud break*.—5 April.

Disease resistance: Moderately resistant to powdery mildew, downy mildew, and anthracnose, and susceptible to black rot. Other disease susceptibilities not known.

Flower:

*Fragrance*.—Sweet, flowery, distinct.

*Sex*.—Hermaphrodite.

*Bloom dates*.—First bloom: 23 May; full bloom: 25 May.

*Flowers per cluster*.—763.

*Inflorescence dimensions*.—Length: 18.8 cm; diameter: 4.9 cm.

*Flower dimensions*.—Length: 0.5 cm; diameter: 0.8 cm.

*Flower shape*.—Length: 0.5 cm; diameter: 0.8 cm. Flower shape is typical of *Euvitis* (bunch) grapes, with flowers having a cohering petal at summit and separating petal at base and petal reflexed after dehiscence from flower.

*Flower longevity*.—Lasts 3-5 days in full bloom.

Stamens:

*Number*.—5.

*Filament color*.—Yellow-green group 145-C.

Pistil:

*Number*.—1.

*Length*.—0.3 cm.

*Color*.—Yellow-green group 144-A.

Pollen:

*Color*.—Yellow-orange group 20-B.

Petal:

*Number*.—5.2 fused petals, form calyptra (flower cap).

*Color*.—Yellow-green group 144-A.

Sepal: None.

Pedicel:

*Dimensions*.—Length: 0.93 cm; diameter: 0.14 cm.

*Color*.—Top: grayed-orange group 174-A; bottom: yellow-green group 144-B.

Fruit:

*Maturity*.—22 August.

*Berry shape*.—Elongated, oval.

*Berry color*.—Skin: yellow-green group 145-A; flesh: yellow-green group 145-A.

*Berry dimensions*.—Diameter at equator: 1.7 cm; diameter at base: 1.1 cm; diameter at apex: 0.9 cm; length: 2.4 cm.

*Berry weight*.—4.5 g.

*Berry texture*.—Non-slipskin; crisp.

*Firmness*.—Very firm.

*Skin thickness*.—0.4 mm.

*Tenacity*.—High.

*Seeds*.—No, small residual seed traces present most years.

*Brush length*.—0.4 cm.

*Juiciness*.—Low.

*Flavor*.—Is fruity derived partially from *V. labrusca*, with some aspects of muscat.

*Storage*.—Fruit storage successful for four weeks, superior to 'Jupiter' (U.S. Plant Pat. No. 13,309).

Juice:

*Color*.—Yellow group 4-D.

*Soluble solids*.—20.0%.

*Titratable acidity*.—0.58 g/L tartaric acid.

*PH*.—3.4.

Seed: Seedless, no seeds present. Seed traces of undeveloped seeds, number per berry: 2, very soft/edible.

Cluster:

*Weight*.—470 g.

*Cluster dimensions*.—Length: 20.0 cm; width: 18.4 cm.

*Berries per cluster*.—128.

*Cluster per vine*.—30.

*Clusters per shoot*.—1.6.

*Peduncle length*.—5.0 cm.

*Peduncle diameter*.—4.16 mm.

*Peduncle color*.—Yellow-green group 145-A (no anthocyanin present).

Use: Fresh-market green table grape with improved vines particularly adapted in the mid- to upper-South.

The cultivar: The new cultivar is a green (white), seedless table grape which provides a significant advancement in fruit crispness and firmness beyond previous Arkansas developments along with having an unique fruity flavor and limited fruit cracking or splitting in an Arkansas environment.

I claim:

1. A new and distinct cultivar of grape plant named 'Compassion', substantially illustrated and described.

* * * * *